(12) United States Patent
Gutelius et al.

(10) Patent No.: US 10,371,238 B2
(45) Date of Patent: Aug. 6, 2019

(54) ADAPTER ASSEMBLY FOR SURGICAL DEVICE

(71) Applicant: Covidien LP, Mansfield, MA (US)

(72) Inventors: Patrick N. Gutelius, Monroe, CT (US); Khalil R. Khouri, Key Biscayne, FL (US); Jeffrey P. Radziunas, Wallingford, CT (US)

(73) Assignee: Covidien LP, Mansfield, MA (US)

( * ) Notice: Subject to any disclaimer, the term of this patent is extended or adjusted under 35 U.S.C. 154(b) by 304 days.

(21) Appl. No.: 15/262,055

(22) Filed: Sep. 12, 2016

(65) Prior Publication Data

US 2017/0102055 A1    Apr. 13, 2017

Related U.S. Application Data

(60) Provisional application No. 62/239,301, filed on Oct. 9, 2015.

(51) Int. Cl.
| | | |
|---|---|---|
| *F16H 19/06* | (2006.01) | |
| *A61B 17/34* | (2006.01) | |
| *A61B 17/115* | (2006.01) | |
| *A61B 17/00* | (2006.01) | |
| *A61B 17/29* | (2006.01) | |

(52) U.S. Cl.
CPC .......... *F16H 19/06* (2013.01); *A61B 17/1155* (2013.01); *A61B 17/3476* (2013.01); *A61B 2017/00398* (2013.01); *A61B 2017/00464* (2013.01); *A61B 2017/00473* (2013.01); *A61B 2017/00477* (2013.01); *A61B 2017/00486* (2013.01); *A61B 2017/2903* (2013.01); *A61B 2017/2905* (2013.01)

(58) Field of Classification Search
CPC .. A61B 2017/00486; A61B 2017/2905; A61B 17/3476; A61B 2017/00477; A61B 2017/00464; F16H 19/06
USPC ............................................................ 606/1
See application file for complete search history.

(56) References Cited

U.S. PATENT DOCUMENTS

| | | |
|---|---|---|
| 2,777,340 A | 1/1957 | Hettwer et al. |
| 2,957,353 A | 10/1960 | Babacz |
| 3,111,328 A | 11/1963 | Di Rito et al. |
| 3,695,058 A | 10/1972 | Keith, Jr. |

(Continued)

FOREIGN PATENT DOCUMENTS

| | | |
|---|---|---|
| CA | 2451558 A1 | 1/2003 |
| CN | 1547454 A | 11/2004 |

(Continued)

OTHER PUBLICATIONS

Extended European Search Report corresponding to counterpart International Application No. EP 14 18 4882.0 dated May 12, 2015.

(Continued)

*Primary Examiner* — Gary Jackson
*Assistant Examiner* — Zahed Kabir

(57) ABSTRACT

An adapter assembly for connecting an end effector to a surgical instrument includes first, second, and third drive assemblies configured for converting rotational motion into linear motion. Each of the second and third drive assemblies includes a pair of rotatable drive shafts for longitudinally advancing and retracting respective second and third drive members.

20 Claims, 10 Drawing Sheets

(56) References Cited

U.S. PATENT DOCUMENTS

| | | |
|---|---|---|
| 3,734,515 A | 5/1973 | Dudek |
| 3,759,336 A | 9/1973 | Marcovitz et al. |
| 4,162,399 A | 7/1979 | Hudson |
| 4,606,343 A | 8/1986 | Conta et al. |
| 4,705,038 A | 11/1987 | Sjostrom et al. |
| 4,722,685 A | 2/1988 | de Estrada et al. |
| 4,823,807 A | 4/1989 | Russell et al. |
| 4,874,181 A | 10/1989 | Hsu |
| 5,129,118 A | 7/1992 | Walmesley |
| 5,129,570 A | 7/1992 | Schulze et al. |
| 5,152,744 A | 10/1992 | Krause et al. |
| 5,301,061 A | 4/1994 | Nakada et al. |
| 5,312,023 A | 5/1994 | Green et al. |
| 5,326,013 A | 7/1994 | Green et al. |
| 5,350,355 A | 9/1994 | Sklar |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen et al. |
| 5,411,508 A | 5/1995 | Bessler et al. |
| 5,413,267 A | 5/1995 | Solyntjes et al. |
| 5,427,087 A | 6/1995 | Ito et al. |
| 5,433,721 A | 7/1995 | Hooven et al. |
| 5,467,911 A | 11/1995 | Tsuruta et al. |
| 5,476,379 A | 12/1995 | Disel |
| 5,487,499 A | 1/1996 | Sorrentino et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,549,637 A | 8/1996 | Crainich |
| 5,553,675 A | 9/1996 | Pitzen et al. |
| 5,562,239 A | 10/1996 | Boiarski et al. |
| 5,564,615 A | 10/1996 | Bishop et al. |
| 5,609,560 A | 3/1997 | Ichikawa et al. |
| 5,626,587 A | 5/1997 | Bishop et al. |
| 5,632,432 A | 5/1997 | Schulze et al. |
| 5,645,209 A | 7/1997 | Green et al. |
| 5,647,526 A | 7/1997 | Green et al. |
| 5,653,374 A | 8/1997 | Young et al. |
| 5,658,300 A | 8/1997 | Bito et al. |
| 5,662,662 A | 9/1997 | Bishop et al. |
| 5,667,517 A | 9/1997 | Hooven |
| 5,693,042 A | 12/1997 | Boiarski et al. |
| 5,704,534 A | 1/1998 | Huitema et al. |
| 5,713,505 A | 2/1998 | Huitema |
| 5,762,603 A | 6/1998 | Thompson |
| 5,779,130 A | 7/1998 | Alesi et al. |
| 5,782,396 A | 7/1998 | Mastri et al. |
| 5,782,397 A | 7/1998 | Koukline |
| 5,792,573 A | 8/1998 | Pitzen et al. |
| 5,797,536 A | 8/1998 | Smith et al. |
| 5,820,009 A | 10/1998 | Melling et al. |
| 5,863,159 A | 1/1999 | Lasko |
| 5,908,427 A | 6/1999 | McKean et al. |
| 5,954,259 A | 9/1999 | Viola et al. |
| 5,964,774 A | 10/1999 | McKean et al. |
| 5,993,454 A | 11/1999 | Longo |
| 6,010,054 A | 1/2000 | Johnson et al. |
| 6,017,354 A | 1/2000 | Culp et al. |
| 6,032,849 A | 3/2000 | Mastri et al. |
| 6,045,560 A | 4/2000 | McKean et al. |
| 6,090,123 A | 7/2000 | Culp et al. |
| 6,126,651 A | 10/2000 | Mayer |
| 6,129,547 A | 10/2000 | Cise et al. |
| 6,165,169 A | 12/2000 | Panescu et al. |
| 6,239,732 B1 | 5/2001 | Cusey |
| 6,241,139 B1 | 6/2001 | Milliman et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp et al. |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,434,507 B1 | 8/2002 | Clayton et al. |
| 6,443,973 B1 | 9/2002 | Whitman |
| 6,461,372 B1 | 10/2002 | Jensen et al. |
| 6,488,197 B1 | 12/2002 | Whitman |
| 6,491,201 B1 | 12/2002 | Whitman |
| 6,533,157 B1 | 3/2003 | Whitman |
| 6,537,280 B2 | 3/2003 | Dinger et al. |
| 6,610,066 B2 | 8/2003 | Dinger et al. |
| 6,611,793 B1 | 8/2003 | Burnside et al. |
| 6,645,218 B1 | 11/2003 | Cassidy et al. |
| 6,654,999 B2 | 12/2003 | Stoddard et al. |
| 6,698,643 B2 | 3/2004 | Whitman |
| 6,699,177 B1 | 3/2004 | Wang et al. |
| 6,716,233 B1 | 4/2004 | Whitman |
| 6,743,240 B2 | 6/2004 | Smith et al. |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,860,892 B1 | 3/2005 | Tanaka et al. |
| 6,899,538 B2 | 5/2005 | Matoba |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,111,769 B2 | 9/2006 | Wales et al. |
| 7,122,029 B2 | 10/2006 | Koop et al. |
| 7,140,528 B2 | 11/2006 | Shelton, IV |
| 7,141,049 B2 | 11/2006 | Stern et al. |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |
| 7,252,660 B2 | 8/2007 | Kunz |
| 7,328,828 B2 | 2/2008 | Ortiz et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |

(56) References Cited

U.S. PATENT DOCUMENTS

| | | |
|---|---|---|
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,900,805 B2 | 3/2011 | Shelton, IV et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Soirica et al. |
| 7,967,179 B2 | 6/2011 | Olson et al. |
| 7,992,758 B2 | 8/2011 | Whitman et al. |
| 8,011,550 B2 | 9/2011 | Aranyi et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,114,118 B2 | 2/2012 | Knodel et al. |
| 8,127,975 B2 | 3/2012 | Olson et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,342,379 B2 | 1/2013 | Whitman et al. |
| 8,348,130 B2 | 1/2013 | Shah et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,403,926 B2 | 3/2013 | Nobis et al. |
| 8,418,904 B2 | 4/2013 | Wenchell et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,523,043 B2 | 9/2013 | Ullrich et al. |
| 8,551,076 B2 | 10/2013 | Duval et al. |
| 8,561,871 B2 | 10/2013 | Rajappa et al. |
| 8,561,874 B2 | 10/2013 | Scirica |
| 8,602,287 B2 | 12/2013 | Yates et al. |
| 8,623,000 B2 | 1/2014 | Humayun et al. |
| 8,627,995 B2 | 1/2014 | Smith et al. |
| 8,632,463 B2 | 1/2014 | Drinan et al. |
| 8,636,766 B2 | 1/2014 | Milliman et al. |
| 8,647,258 B2 | 2/2014 | Aranyi et al. |
| 8,652,121 B2 | 2/2014 | Quick et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,715,306 B2 | 5/2014 | Faller et al. |
| 8,758,391 B2 | 6/2014 | Swayze et al. |
| 8,806,973 B2 | 8/2014 | Ross et al. |
| 8,808,311 B2 | 8/2014 | Heinrich et al. |
| 8,820,605 B2 | 9/2014 | Shelton, IV |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,888,762 B2 | 11/2014 | Whitman |
| 8,893,946 B2 | 11/2014 | Boudreaux et al. |
| 8,899,462 B2 | 12/2014 | Kostrzewski et al. |
| 8,905,289 B2 | 12/2014 | Patel et al. |
| 8,919,630 B2 | 12/2014 | Milliman |
| 8,931,680 B2 | 1/2015 | Milliman |
| 8,939,344 B2 | 1/2015 | Olson et al. |
| 8,950,646 B2 | 2/2015 | Viola |
| 8,960,519 B2 | 2/2015 | Whitman et al. |
| 8,961,396 B2 | 2/2015 | Azarbarzin et al. |
| 8,967,443 B2 | 3/2015 | McCuen |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,016,545 B2 | 4/2015 | Aranyi et al. |
| 9,023,014 B2 | 5/2015 | Chowaniec et al. |
| 9,033,868 B2 | 5/2015 | Whitman et al. |
| 9,055,943 B2 | 6/2015 | Zemlok et al. |
| 9,064,653 B2 | 6/2015 | Prest et al. |
| 9,072,515 B2 | 7/2015 | Hall et al. |
| 9,113,847 B2 | 8/2015 | Whitman et al. |
| 9,113,875 B2 | 8/2015 | Viola et al. |
| 9,113,876 B2 | 8/2015 | Zemlok et al. |
| 9,113,899 B2 | 8/2015 | Garrison et al. |
| 9,216,013 B2 | 12/2015 | Scirica et al. |
| 9,241,712 B2 | 1/2016 | Lemlok et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 2001/0031975 A1 | 10/2001 | Whitman et al. |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0165794 A1 | 9/2003 | Matoba |
| 2004/0034369 A1 | 2/2004 | Sauer et al. |
| 2004/0111012 A1 | 6/2004 | Whitman |
| 2004/0133189 A1 | 7/2004 | Sakurai |
| 2004/0153124 A1 | 8/2004 | Whitman |
| 2004/0176751 A1 | 9/2004 | Weitzner et al. |
| 2004/0193146 A1 | 9/2004 | Lee et al. |
| 2005/0125027 A1 | 6/2005 | Knodel et al. |
| 2005/0131442 A1 | 6/2005 | Yachia et al. |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0259073 A1 | 11/2006 | Miyamoto et al. |
| 2006/0278680 A1 | 12/2006 | Viola et al. |
| 2006/0284730 A1 | 12/2006 | Schmid et al. |
| 2007/0023476 A1 | 2/2007 | Whitman et al. |
| 2007/0023477 A1 | 2/2007 | Whitman et al. |
| 2007/0029363 A1 | 2/2007 | Popov |

(56) References Cited

U.S. PATENT DOCUMENTS

| | | |
|---|---|---|
| 2007/0055219 A1* | 3/2007 | Whitman .......... A61B 17/00234 606/1 |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0175961 A1 | 8/2007 | Shelton et al. |
| 2007/0270784 A1 | 11/2007 | Smith et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0147089 A1 | 6/2008 | Loh et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0012533 A1 | 1/2009 | Barbagli et al. |
| 2009/0090763 A1 | 4/2009 | Zemlok et al. |
| 2009/0099876 A1 | 4/2009 | Whitman |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0209946 A1 | 8/2009 | Swayze et al. |
| 2009/0209990 A1 | 8/2009 | Yates et al. |
| 2009/0254094 A1 | 10/2009 | Knapp et al. |
| 2009/0299141 A1 | 12/2009 | Downey et al. |
| 2010/0023022 A1 | 1/2010 | Zeiner et al. |
| 2010/0069942 A1 | 3/2010 | Shelton, IV |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2011/0071508 A1 | 3/2011 | Duval et al. |
| 2011/0077673 A1 | 3/2011 | Grubac et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174009 A1 | 7/2011 | Iizuka et al. |
| 2011/0174099 A1 | 7/2011 | Ross et al. |
| 2011/0184245 A1 | 7/2011 | Xia et al. |
| 2011/0204119 A1 | 8/2011 | McCuen |
| 2011/0218522 A1 | 9/2011 | Whitman |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0074199 A1 | 3/2012 | Olson et al. |
| 2012/0089131 A1 | 4/2012 | Zemlok et al. |
| 2012/0104071 A1* | 5/2012 | Bryant ............ A61B 17/07207 227/175.1 |
| 2012/0116368 A1 | 5/2012 | Viola |
| 2012/0143002 A1 | 6/2012 | Aranyi et al. |
| 2012/0172924 A1 | 7/2012 | Allen, IV |
| 2012/0211542 A1 | 8/2012 | Racenet |
| 2012/0223121 A1 | 9/2012 | Viola et al. |
| 2012/0245428 A1 | 9/2012 | Smith et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0093149 A1 | 4/2013 | Saur et al. |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236174 A1 | 8/2014 | Williams et al. |
| 2014/0276932 A1* | 9/2014 | Williams ............... A61B 17/29 606/130 |
| 2014/0299647 A1 | 10/2014 | Scirica et al. |
| 2014/0303668 A1 | 10/2014 | Nicholas et al. |
| 2014/0358129 A1* | 12/2014 | Zergiebel ............ A61B 17/28 606/1 |
| 2014/0361068 A1 | 12/2014 | Aranyi et al. |
| 2014/0365235 A1 | 12/2014 | DeBoer et al. |
| 2014/0373652 A1 | 12/2014 | Zergiebel et al. |
| 2015/0014392 A1 | 1/2015 | Williams et al. |
| 2015/0048144 A1 | 2/2015 | Whitman |
| 2015/0076205 A1 | 3/2015 | Zergiebel |
| 2015/0080912 A1 | 3/2015 | Sapre |
| 2015/0112381 A1 | 4/2015 | Richard |
| 2015/0122870 A1 | 5/2015 | Zemlok et al. |
| 2015/0133224 A1 | 5/2015 | Whitman et al. |
| 2015/0150547 A1 | 6/2015 | Ingmanson et al. |
| 2015/0150574 A1 | 6/2015 | Richard et al. |
| 2015/0157320 A1 | 6/2015 | Zergiebel et al. |
| 2015/0157321 A1 | 6/2015 | Zergiebel et al. |
| 2015/0164502 A1 | 6/2015 | Richard et al. |
| 2015/0201931 A1 | 7/2015 | Zergiebel et al. |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1* | 11/2015 | Kostrzewski ...... A61B 17/0469 606/144 |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0106406 A1* | 4/2016 | Cabrera ............ A61B 17/1155 606/1 |
| 2016/0113648 A1 | 4/2016 | Zergiebel et al. |
| 2016/0113649 A1 | 4/2016 | Zergiebel et al. |
| 2016/0324520 A1* | 11/2016 | Marczyk .......... A61B 17/07207 |

FOREIGN PATENT DOCUMENTS

| | | |
|---|---|---|
| CN | 1957854 A | 5/2007 |
| CN | 101495046 A | 7/2009 |
| CN | 102247182 A | 11/2011 |
| DE | 102008053842 A1 | 5/2010 |
| EP | 0705571 A1 | 4/1996 |
| EP | 1563793 A1 | 8/2005 |
| EP | 1769754 A1 | 4/2007 |

(56) References Cited

FOREIGN PATENT DOCUMENTS

| EP | 1897501 A1 * | 3/2008 | ........... A61B 17/072 |
|----|---|---|---|
| EP | 1982657 A2 | 10/2008 | |
| EP | 2233081 A2 | 9/2010 | |
| EP | 2316345 A1 | 5/2011 | |
| EP | 2668910 A2 | 12/2013 | |
| EP | 2687166 A2 | 1/2014 | |
| ES | 2333509 A1 | 2/2010 | |
| JP | 2005-125075 A | 5/2005 | |
| KR | 20120022521 A | 3/2012 | |
| WO | 2011/108840 A2 | 9/2011 | |
| WO | 2012/040984 A1 | 4/2012 | |

OTHER PUBLICATIONS

Canadian Office Action corresponding to counterpart International Application No. CA 2640399 dated May 7, 2015.
Japanese Office Action corresponding to counterpart International Application No. JP 2011-197365 dated Mar. 23, 2015.
Japanese Office Action corresponding to counterpart International Application No. JP 2011-084092 dated May 20, 2015.
Japanese Office Action corresponding to counterpart International Application No. JP 2014-148482 dated Jun. 2, 2015.
Extended European Search Report corresponding to counterpart International Application No. EP 14 18 9358.6 dated Jul. 8, 2015.
Extended European Search Report corresponding to counterpart International Application No. EP 14 19 6148.2 dated Apr. 23, 2015.
Partial European Search Report corresponding to counterpart International Application No. EP 14 19 6704.2 dated May 11, 2015.
Australian Office Action corresponding to counterpart International Application No. AU 2010241367 dated Aug. 20, 2015.
Partial European Search Report corresponding to counterpart International Application No. EP 14 19 9783.3 dated Sep. 3, 2015.
Extended European Search Report corresponding to counterpart International Application No. EP 15 16 9962.6 dated Sep. 14, 2015.
Extended European Search Report corresponding to International Application No. EP 15 15 1076.5 dated Apr. 22, 2015.
Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, dated Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 38071 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
Office Action corresponding to counterpart Int'l Appln. No. CN 201310369318.2 dated Jun. 28, 2016.
Chinese Office Action (with English translation), dated Jul. 4, 2016, corresponding to Chinese Patent Application No. 2015101559718; 23 total pages.
European Search Report EP 15 156 035.6 dated Aug. 10, 2016.
European Search Report dated Feb. 10, 2017, issued in EP Appln. No. 16192781.

* cited by examiner

ADAPTER ASSEMBLY FOR SURGICAL DEVICE

CROSS-REFERENCE TO RELATED APPLICATIONS

This application claims the benefit of and priority to U.S. Provisional Patent Application No. 62/239,301 filed Oct. 9, 2015, the entire disclosure of which is incorporated by reference herein.

BACKGROUND

1. Technical Field

The present disclosure relates generally to powered surgical devices. More specifically, the present disclosure relates to adapter assemblies for selectively connecting end effectors to actuation units of powered surgical devices.

2. Background of Related Art

Powered devices for use in surgical procedures typically convert rotational motion from a handle assembly to linear motion for effectuating one or more functions, e.g., clamping, stapling, cutting. To permit reuse of the handle assemblies of these powered surgical devices and so that the handle assembly may be used with a variety of end effectors, adapter assemblies have been developed for selective attachment to the handle assemblies and to a variety of end effectors. Following use, the adapter assembly may be disposed of along with the end effector.

SUMMARY

An adapter assembly for operably connecting an end effector to a powered surgical instrument is provided. The adapter assembly includes a drive coupling assembly and first, second, and third drive assemblies. The first drive assembly is operably connected to the drive coupling assembly and includes a rotatable drive shaft. The second drive assembly is operably connected to the drive coupling assembly and includes a first pair of rotatable drive shafts. A first shaft of the first pair of rotatable drive shafts rotates in a first direction and a second shaft of the first pair of rotatable drive shafts rotates in a second direction. The third drive assembly is operably connected to the drive coupling assembly. The third drive assembly includes a second pair of rotatable drive shafts. A first shaft of the second pair of rotatable drive shafts rotates in a first direction and a second shaft of the second pair of rotatable drive shafts rotates in a second direction.

In one embodiment, the adapter assembly further includes a trocar member. Rotation of the rotatable drive shaft of the first drive assembly may effect longitudinal movement of the trocar member. The adapter assembly may further include a first pusher assembly supported in a distal end of the adapter assembly. Rotation of the first pair of rotatable drive shafts may effect longitudinal movement of the first pusher assembly. The adapter assembly may further include a second pusher assembly supported in a distal end of the adapter assembly, wherein rotation of the second pair of rotatable drive shafts effects longitudinal movement of a second pusher assembly. The second pusher assembly may be nested within the first pusher assembly.

In other embodiments, each of the first, second, and/or third drive assemblies of the adapter assembly may include a high ratio transmission assembly. The first, second, and/or third high ratio transmission assemblies may be one of a harmonic gear system or a planetary gear system. The harmonic gear system may be one of an orbital gear system or a yoked sun orbital gear system.

The adapter assembly may further include an outer sleeve. Each of the first, second, and third drive assemblies may extend through the outer sleeve. The outer sleeve may be flexible. The coupling assembly may be configured for operable connection to a handle assembly. The first and second shafts of the first pair of rotatable drive shafts of the second drive assembly are radially spaced equidistant from the longitudinal axis of the first drive assembly. The first and second shafts of the second pair of rotatable drive shafts are radially spaced equidistant from the longitudinal axis of the first drive assembly.

In embodiments, an input load from a handle assembly is equally distributed between the first and second shafts of the first pair of rotatable drive shafts during operation of the second drive assembly. Similarly, an input load from a handle assembly is equally distributed between the first and second shafts of the second pair of rotatable drive shafts during operation of the third drive assembly.

BRIEF DESCRIPTION OF THE DRAWINGS

Embodiments of the present disclosure are described herein with reference to the accompanying drawings, wherein.

DETAILED DESCRIPTION OF EMBODIMENTS

Figure 1:
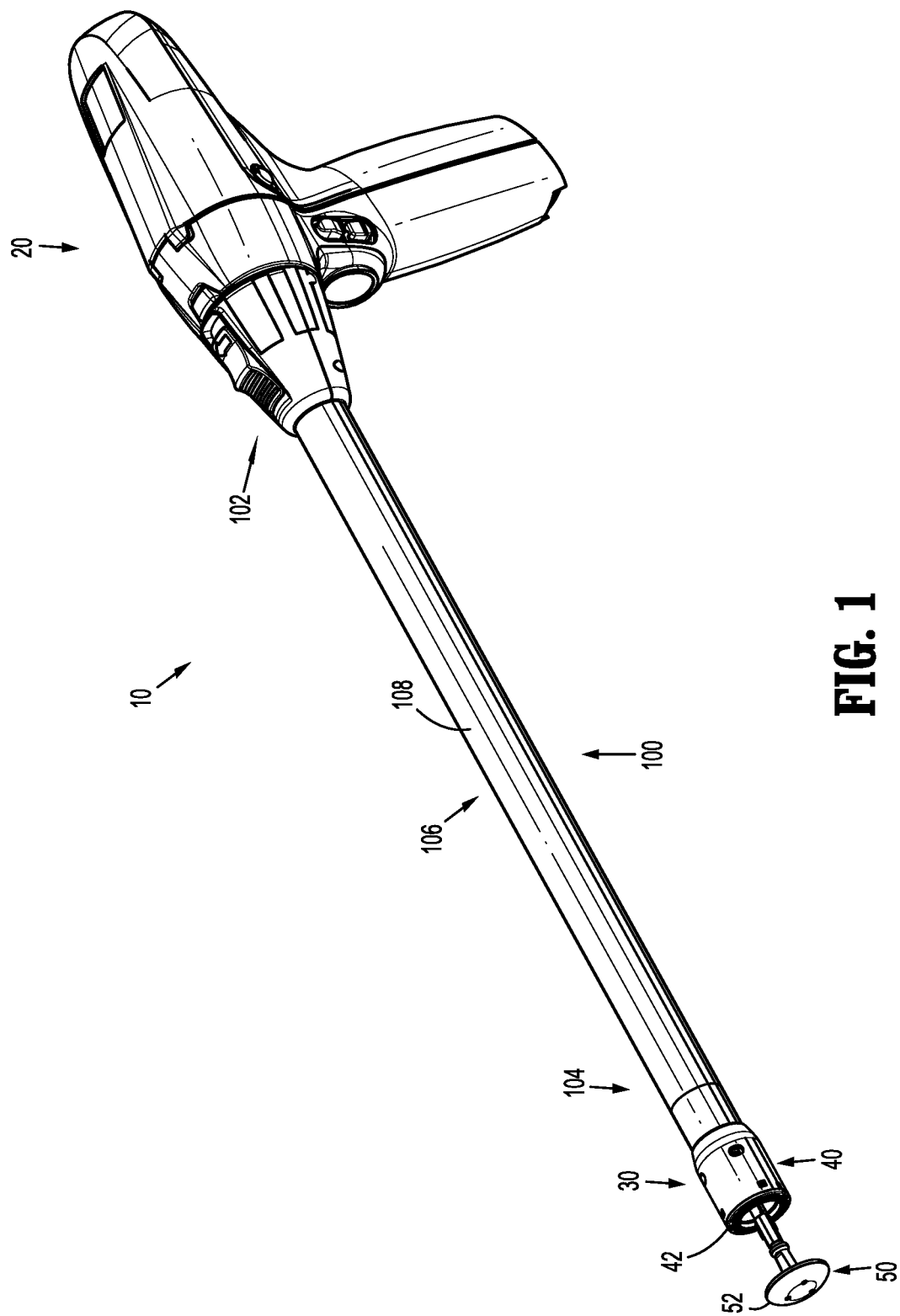
FIG. 1 is a perspective view of an adapter assembly, in accordance with an embodiment of the present disclosure, an exemplary electromechanical surgical device, and an exemplary end effector.

Embodiments of the presently disclosed adapter assembly for surgical devices and/or handle assemblies are described in detail with reference to the drawings, in which like reference numerals designate identical or corresponding elements in each of the several views. As used herein the term "distal" refers to that portion of the adapter assembly or surgical device, or component thereof, farther from the user, while the term "proximal" refers to that portion of the adapter assembly or surgical device, or component thereof, closer to the user.

Figure 2:
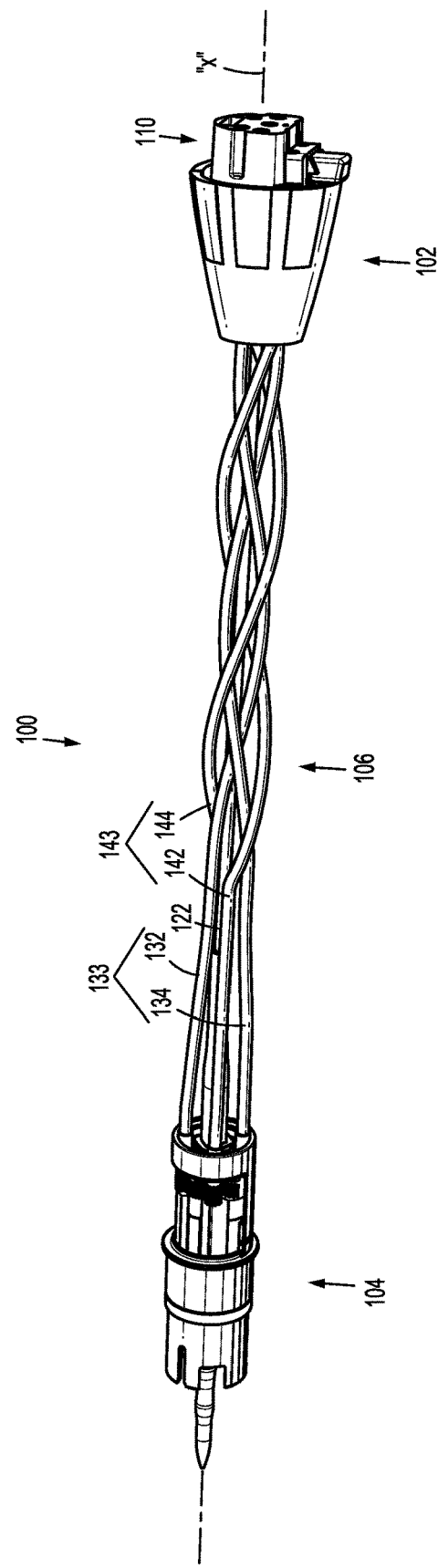
FIG. 2 is a side perspective view of the adapter assembly of FIG. 1, with the outer sleeve removed.

With reference to FIGS. 1 and 2, an adapter assembly in accordance with an embodiment of the present disclosure, shown generally as adapter assembly 100, is configured for selective connection to a powered handheld electromechanical instrument shown, generally as handle assembly 20. As illustrated in FIG. 1, the handle assembly 20 is configured for selective connection with the adapter assembly 100, and, in turn, the adapter assembly 100 is configured for selective connection with a tool assembly or end effector, e.g. tool assembly 30, which may, in exemplary embodiments, include a loading unit 40 and an anvil assembly 50, for applying a circular array of staples (not shown) to tissue (not shown). The handle assembly 20, the adapter assembly 100, and the tool assembly 30 form a surgical stapling device 10. Although shown and described for use with a circular stapling loading unit, it is envisioned that the aspects of the present disclosure may be modified for use with stapling assembly have alternative configurations.

For a detailed description of the structure and function of an exemplary handle assembly, please refer to commonly owned U.S. Pat. Appl. Publ. No. 2012/0253329, the content of which is incorporated by reference herein in its entirety.

With continued reference to FIG. 2, the adapter assembly 100 includes a proximal portion 102 configured for operable connection to the handle assembly 20 (FIG. 1), a distal portion 104 configured for operable connection to the tool assembly 30 (FIG. 1), and an intermediate portion 106 operably connecting the proximal and distal portions 102, 104. The proximal portion 102 of the adapter assembly 100 includes a coupling assembly 110 receivable within the handle assembly 10 for operatively connecting first, second, and third drive shafts (not shown) of the handle assembly 20 (FIG. 1) with the adapter assembly 100. For a detailed description of an exemplary coupling assembly, please refer to commonly owned U.S. Provisional Patent Application Ser. No. 62/066,518 ("the '518 application"), filed Oct. 21, 2014, the contents of which are incorporated herein by reference in their entirety.

First, second, and third drive assemblies 120, 130, 140 (FIG. 7) extend from the coupling assembly 110, through an outer sleeve 108 (FIG. 1) of the intermediate portion 106, and to an actuation assembly 150 (FIGS. 2 and 6) disposed in the distal portion 104 of the adapter assembly 100. As will be described in further detail below, the first drive assembly 120 operates to effect a first function, e.g., clamping of tissue, of the loading unit 40 (FIG. 1). The second drive assembly 130 operates to effect a second function, e.g., stapling of tissue, of the loading unit 40 (FIG. 1). The third drive assembly 140 operates to effect a third function, e.g., cutting of tissue, of the loading unit 40 (FIG. 1).

Figure 3:
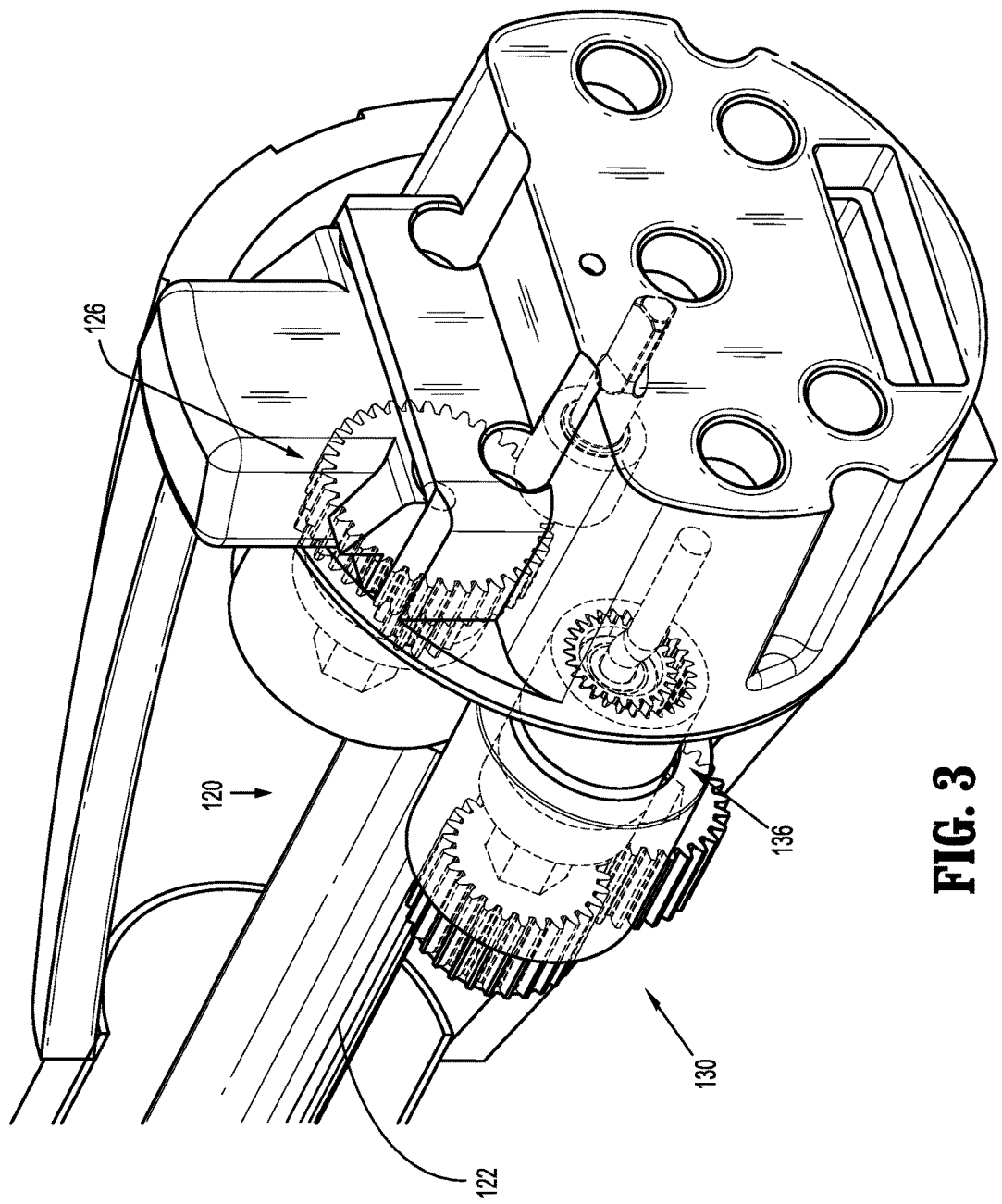
FIG. 3 is a perspective end view of a proximal end of the adapter assembly of FIG. 1.

With reference to FIGS. 2 and 3, the first drive assembly 120 extends through the proximal and intermediate portions 102, 106 of the adapter assembly 100 and includes an elongate shaft 122. The first drive assembly 120 is operably connected to the first drive shaft (not shown) of the handle assembly 20. As will be described in further detail below, rotation of the elongate shaft 122 causes longitudinal movement, i.e., advancement and retraction, of a trocar member 164 of a trocar assembly 160 of the actuation assembly 150 (FIG. 7) disposed in the distal portion 104 of the adapter assembly 100.

Figure 7:
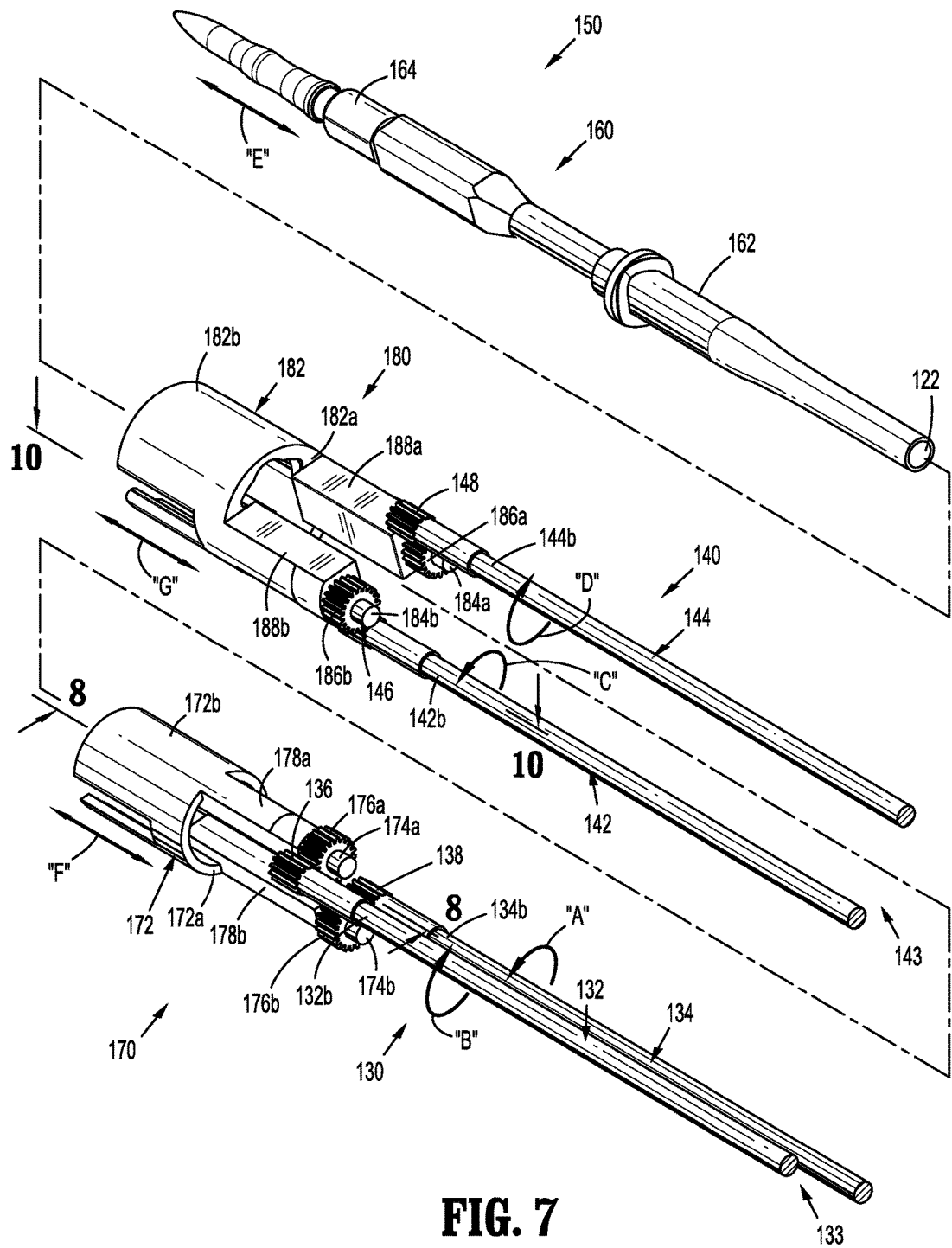
FIG. 7 is a perspective view, with parts separated, of an actuation assembly of the adapter assembly of FIG. 1.

The second drive assembly 130 extends through the proximal and intermediate portions 102, 106 of the adapter assembly 100 and includes first and second rotatable flexible drive shafts 132, 134 of a first pair of drive shafts 133 (FIG. 7). The first and second rotatable flexible drive shafts 132, 134 of the first pair of drive shafts 133 are radially offset an equal distance, i.e., equidistant, from a longitudinal axis "x" (FIG. 2) of the adapter assembly 100. The second drive assembly 130 is operably connectable to the second drive shaft (not shown) of the handle assembly 20. As will be described in further detail below, rotation of the first pair of drive shafts 133 causes longitudinal movement, i.e., advancement and retraction, of a first pusher assembly 170 (FIG. 7) of the actuation assembly 150 (FIG. 7) disposed in the distal portion 104 of the adapter assembly 100.

The third drive assembly 140 (FIG. 7) extends through the proximal and intermediate portions 102, 106 of the adapter assembly 100 and includes first and second rotatable flexible drive shafts 142, 144 of a second pair of drive shafts 143 (FIG. 7). The first and second rotatable flexible drive shafts 142, 144 of the second pair of drive shafts 143 are radially offset an equal distance, i.e., equidistant, from a longitudinal axis "x" (FIG. 2) of the adapter assembly 100. The third drive assembly 140 is operably connectable to the third drive shaft (not shown) of the handle assembly 20. As will be described in further detail below, rotation of the second pair of drive shafts 143 causes longitudinal movement, i.e., advancement and retraction, of a second pusher assembly 180 (FIG. 7) of the actuation assembly 150 (FIG. 7) disposed in the distal portion 104 of the adapter assembly 100.

Figure 4:
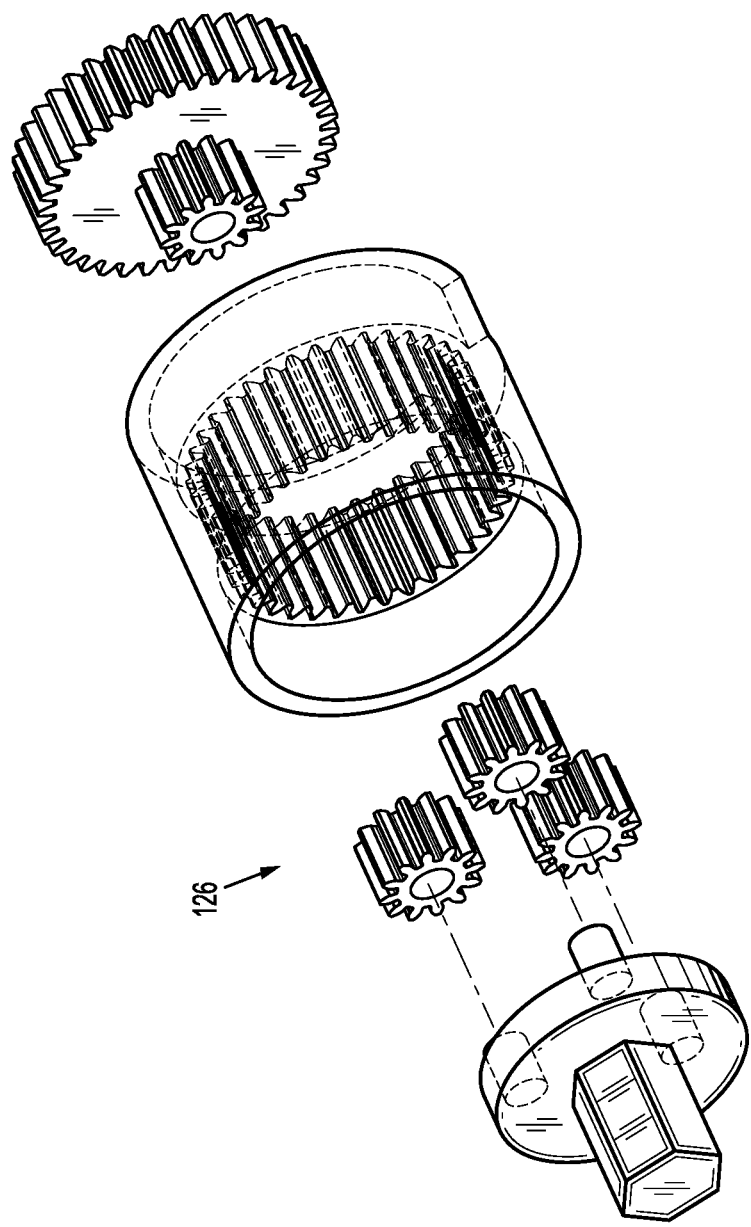
FIG. 4 is a perspective view, with parts separated, of a planetary gear system of the adapter assembly of FIG. 1.
Figure 5A:
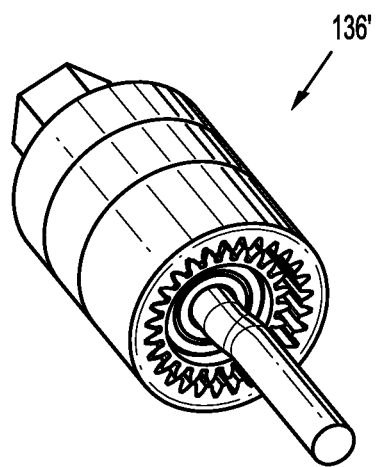
FIG. 5A is a perspective view of an orbital sun harmonic gear system of the adapter assembly of FIG. 1.
Figure 5B:
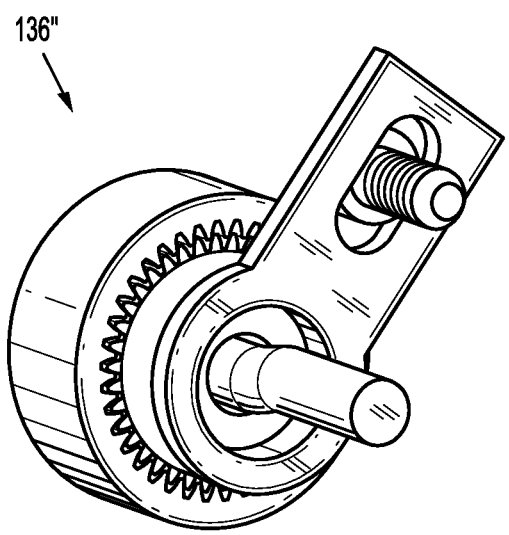
FIG. 5B is a perspective view of a yoked sun harmonic gear system of FIG. 1.

With particular reference to FIG. 3, disposed between the coupling assembly 110 and the elongate flexible shaft 122 of the first drive assembly 120 is a first high ratio transmission assembly 126, i.e., a planetary gear system (FIG. 4). Disposed between the coupling assembly 110 and the first pair of drive shafts 133 (FIG. 7) of the second drive assembly 130 is a second high ratio transmission assembly 136, e.g., a harmonic gear system, such as an orbital gear system 136' (FIG. 5A) or yoked sun orbital gear system 136" (FIG. 5B). A third high ratio transmission assembly (not shown) is disposed between the coupling assembly 110 and the second pair of drive shafts 143.

The high ratio transmission assemblies 126, 136 convert the high speed, low torque rotary input from the handle assembly 20 (FIG. 1) to lower speed, higher torque output for use in effecting actuation of the tool assembly 30 (FIG. 1). Although the first high ratio transmission assembly 126 is shown as a planetary gear system and the second high ratio transmission assembly 136 is shown as a harmonic gear system, it is envisioned that the first, second, and third high ratio transmission assemblies may be the same, and/or may include alternative gear systems for converting the high speed, low torque rotary input from the handle assembly 20 to the low speed, high torque output necessary for effectuating actuation of the tool assembly 30 (FIG. 1). For a detailed description of an exemplary planetary gear system, please refer to the '518 application, the content of which was previously incorporated by reference.

Each of the second and third drive assemblies 130, 140 includes a direction idler (not shown) for changing the direction of one of each of the first and second rotatable flexible shafts 132, 134, 142, 144 of the respective first and second pairs of drive shafts 133, 143. For example, as shown in FIG. 7, the first rotatable flexible shaft 132 of the first pair of drive shafts 133 turns in a counter-clockwise direction, as indicated by arrow "A", and the second rotatable flexible shaft 134 of the first pair of drive shafts 133 turns in a clockwise direction, as indicated by arrow "B". Similarly, the first rotatable flexible shaft 142 of the second pair of drive shafts 143 turns in a counter-clockwise direction, as indicated by arrow "C", and the second rotatable flexible shaft 144 of the second pair of drive shafts 143 turns in a clockwise direction, as indicated by arrow "D".

By changing the direction of rotation of one of each of the first and second rotatable flexible shafts 132, 134, 142, 144 of the respective first and second pairs of drive shafts 133, 143, and by equally radially offsetting the first and second rotatable flexible shafts 132, 134, 142, 144 from a central longitudinal axis "x" of adapter assembly 100, the moments experienced within the adapter assembly 100 are negated, thereby providing a balanced load delivery. The counter torque pairing eliminates the need for a robust support sheath for high loads, thereby allowing for a more flexible intermediate portion 106 (FIG. 1) of the adapter assembly 100. The lesser loads experienced by the adapter assembly 100 during operation also allow for a reduced length of the intermediate portion 106 of adapter assembly 100 needing to be rigid.

The first and second rotatable flexible shafts 132, 134, 142, 144 of the respective first and second pairs of drive shafts 133, 143 each transfer half of an input load from the handle assembly 20 to the distal portion 104 of the adapter assembly 100. In this manner, a second input load received from the handle assembly 20 through the second connector 126 is split equally between the first and second rotatable flexible shafts 132, 134 of the first pair of drive shafts 133. Similarly, a third input load received from the handle assembly 20 through the third connector 128 is split equally between the first and second rotatable flexible shafts 142, 144 of the second pair of drive shafts 143. Further, by splitting the load between the first and second rotatable flexible shafts 132, 134, 142, 144 of the respective first and second pairs of drive shafts 133, 143 rather than through an equivalent single drive shaft (not shown), the diameter of each of the first and second rotatable shafts 132, 134, 142, 144 is smaller than the diameter of the single drive shaft. A smaller diameter shaft allows for greater flexibility of the flexible intermediate portion 106 of the adapter assembly 100 over an intermediate portion (not shown) of an adapter assembly (not shown) including an equivalent single drive cable (not shown).

As shown in FIG. 2, the first and second rotatable flexible shafts 132, 134, 142, 144 of the respective first and second pairs of drive shafts 133, 143 of the first and second drive assemblies 130, 140, respectively, each forms a helical configuration along the length thereof. The helical configuration of each of the first and second rotatable flexible shafts 132, 134, 142, 144 permits for great flexibility of a flexible intermediate portion 106 of the adapter assembly 100. More particularly, the helical configuration of the first and second rotatable flexible shafts 132, 134, 142, 144 provides slack in each of the first and second rotatable flexible shafts 132, 134, 142, 144 which accommodates the lengthening and shortening of the flexible intermediate portion 106 of the adapter assembly 100 as the adapter assembly 100 is flexed during use of the surgical stapling instrument 10 (FIG. 1).

Figure 6:
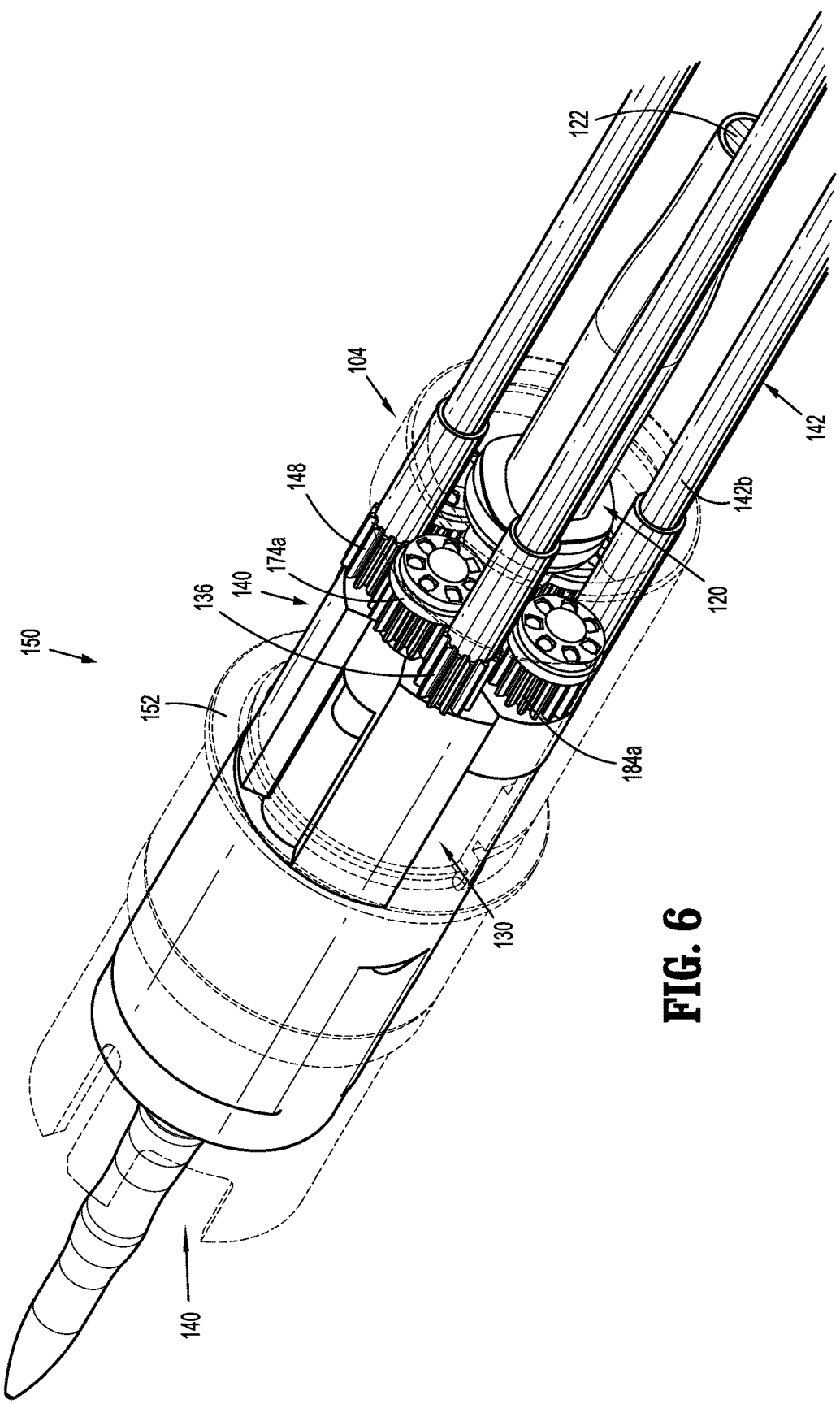
FIG. 6 is a perspective view of a distal end of the adapter assembly of FIG. 1, with the sleeve removed and a housing shown in phantom.

With reference now to FIGS. 6 and 7, as noted above, the trocar assembly 160 of the actuation assembly 150 is disposed on a distal end of the elongate flexible drive shaft 122 of the first drive assembly 120. The trocar assembly 160 is received within an actuation housing 152 (FIG. 6) of the actuation assembly 150, and includes a base member 162, and a trocar member 164 extendable relative to the base member 162. Although not shown, the trocar member 164 includes an internally threaded portion that is received within the base member 162 that engages an externally threaded distal end (not shown) of the elongate flexible shaft 122. Rotation of the elongate flexible shaft 122 causes the trocar member 164 to move longitudinally, as indicated by arrows "E" in FIG. 7, relative to the base member 162. The trocar member 164 and the elongate flexible shaft 122 may be disposed along the longitudinal axis "x" (FIG. 2) of the adapter assembly 100. For a detailed description of an exemplary trocar assembly, please refer to the '518 application, the contents of which were previously incorporated herein by reference.

With continued reference to FIGS. 6 and 7, first and second drive gears 136, 138 are disposed on distal ends 132a, 134a, respectively, of the respective first and second rotatable flexible shafts 132, 134 of the first pair of drive shafts 133, and first and second drive gears 146, 148 are disposed on distal ends 142a, 144a, respectively, of the respective first and second rotatable flexible shafts 142, 144 of the second pair of drive shafts 143. Rotation of the first and second rotatable flexible shafts 132, 134, 142, 144 of the respective first and second pairs of drive shafts 133, 143 causes rotation of the respective first and second drive gears 136, 138, 146, 148. As noted above, an idler gear (not shown) disposed between the coupling assembly 110 of the adapter assembly 100 and each the first and second rotatable flexible shafts 132, 134, 142, 144 of the second and third drive assemblies 130, 140 causes one each of the first and second rotatable flexible shafts 132, 134, 142, 144, respectively, to rotate opposite the other of the respective first and second paired shafts 132, 134, 142, 144.

With continued reference to FIG. 7, the actuation assembly 150 further includes a first pusher assembly 170 and a second pusher assembly 180. The first pusher assembly 170 includes a first pusher member 172 received within the actuation housing 152 and about the trocar assembly 160, and the second pusher assembly 180 includes a second pusher member 182 received within the actuation housing 152 and about the first pusher assembly 170. The second pusher member 182 is received within the first pusher member 172, and the trocar assembly 160 extends through the first and second pusher members 172, 182. In this manner, the first and second pusher members 172, 182 and the trocar assembly 160 are nested. The first and second pusher member 172, 182 are configured for independent longitudinal movement relative to the actuation housing 152 (FIG. 6) to effect respective second and third functions of the loading unit 40 (FIG. 1).

Figure 8:
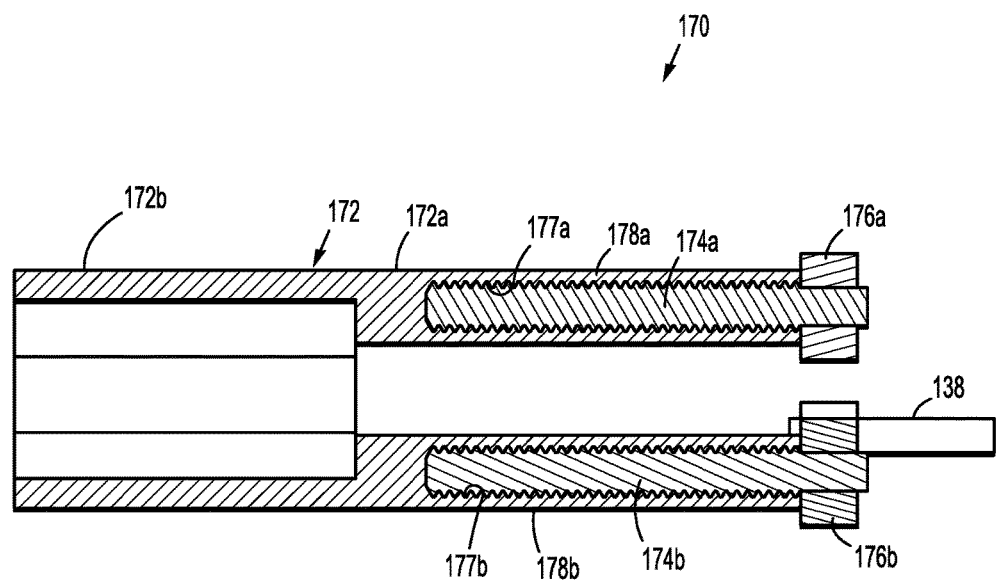
FIG. 8 is a cross-sectional side view of a first pusher assembly of the actuation assembly of FIG. 7 taken along line 8-8, in a first or retracted position.
Figure 9:
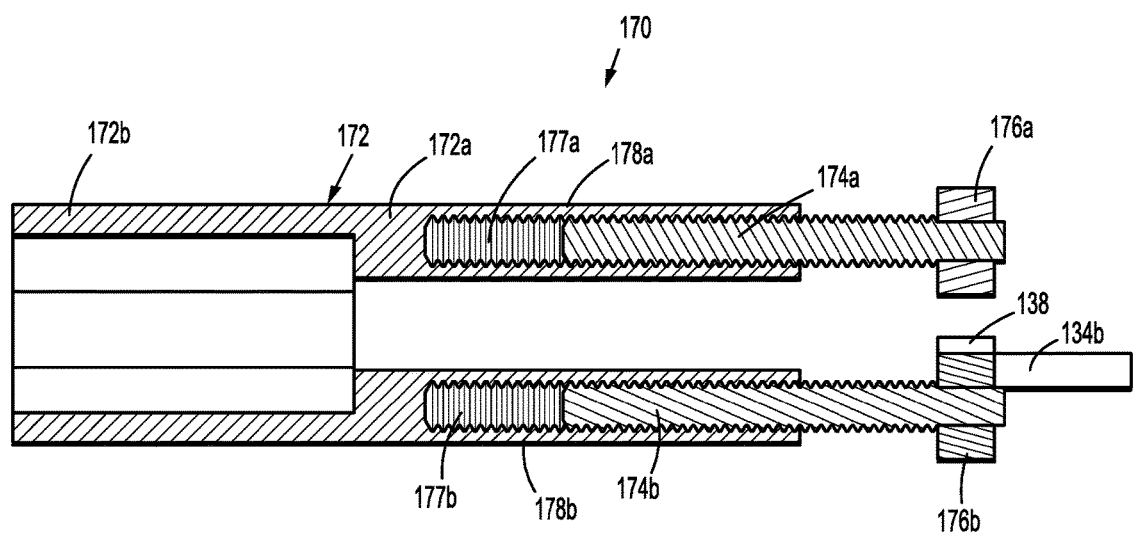
FIG. 9 is a cross-sectional side view of the first pusher assembly of the actuation assembly of FIG. 8, in a second or advanced position.

With additional reference to FIGS. 8 and 9, the first pusher assembly 170 of the actuation assembly 150 includes the first pusher member 172, first and second drive shafts 174a, 174b operably extendable from a proximal end 172a of the first pusher member 172, and first and second drive gears 176a, 176b supported on respective first and second drive shafts 174a, 174b. In particular, the proximal end 172a of the first pusher member 172 of the first pusher assembly 170 includes first and second extensions or shafts 178a, 178b. The first extension 178a defines a threaded passageway 177a wherein the threads are formed in a first direction for receiving a threaded portion of the first drive shaft 174a, and the second extension 178b defines a threaded passageway 177b wherein the threads are formed in a second direction for receiving a threaded portion of the second drive shaft 174b.

With continued reference to FIGS. 8 and 9, the first pusher assembly 170 of the actuation assembly 150 is disposed within the distal portion 104 (FIG. 6) of the adapter assembly 100 such that the first and second drive gears 176a, 176b on the respective first and second drive shafts 174a, 174b engage the respective first and second drive gears 136 (FIG. 7), 138 of the respective first pair of drive shafts 133 of the second drive assembly 130. As noted above, an idler gear (not shown) engages one of the first and second rotatable flexible drive shafts 132, 134 of the first pair of drive shafts 133 to cause the rotation of the first and second rotatable flexible drive shafts 132, 134 in opposite directions, as indicated by arrows "A" and "B" in FIG. 7.

Rotation of the first drive gear 176a in the first direction, simultaneous with rotation of the second drive gear 176b in a second direction, causes longitudinal movement of the first pusher member 172, as indicated by arrow "F" in FIG. 7. More particularly, as the first drive gear 176a rotates the first drive shaft 174a in the first direction, and the second drive gear 176b rotates the second drive gear 174b in the second direction, engagement between the threaded first and second drive shafts 174a, 174b and the respective threaded passageways 177a, 177b of the respective first and second extensions 178a, 178b causes the first pusher member 172 to move distally, i.e., advance. Conversely, as the first drive gear 176a rotates the first drive shaft 174a in the second direction, and the second drive gear 176b rotates the second drive gear 174b in the first direction, engagement between the threaded first and second drive shafts 174a, 174b, and the respective threaded passageways 177a, 177b of the respective first and second extensions 178a, 178b causes the pusher member 172 to move proximally, i.e., retract.

Distal movement of the first pusher member 172 of the first pusher assembly 170 effects actuation of a loading unit, e.g., loading unit 40 (FIG. 1) of the surgical stapling device 10 (FIG. 1). For example, distal movement of the first pusher member 172 causes advancement of a staple pusher (not shown) for stapling tissue (not shown). Conversely, proximal movement of the first pusher member 172 of the first pusher assembly 170 returns the first pusher member 172 to its initial position. In some embodiments, proximal movement of the first pusher member 172 permits separation of the loading unit (not shown) from the adapter assembly 100.

Figure 10:
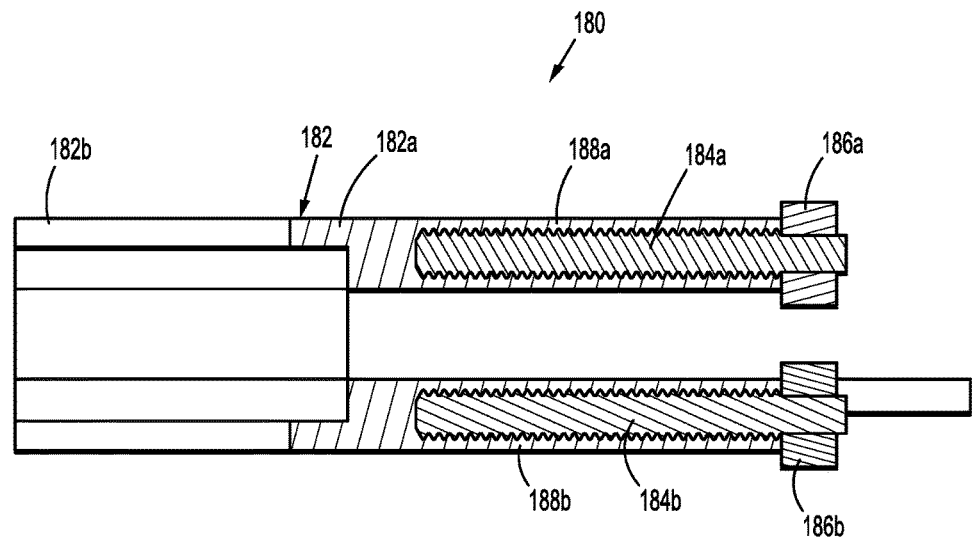
FIG. 10 is a cross-sectional side view of a first pusher assembly of the actuation assembly of FIG. 7 taken along line 8-8, in a first or retracted position.
Figure 11:
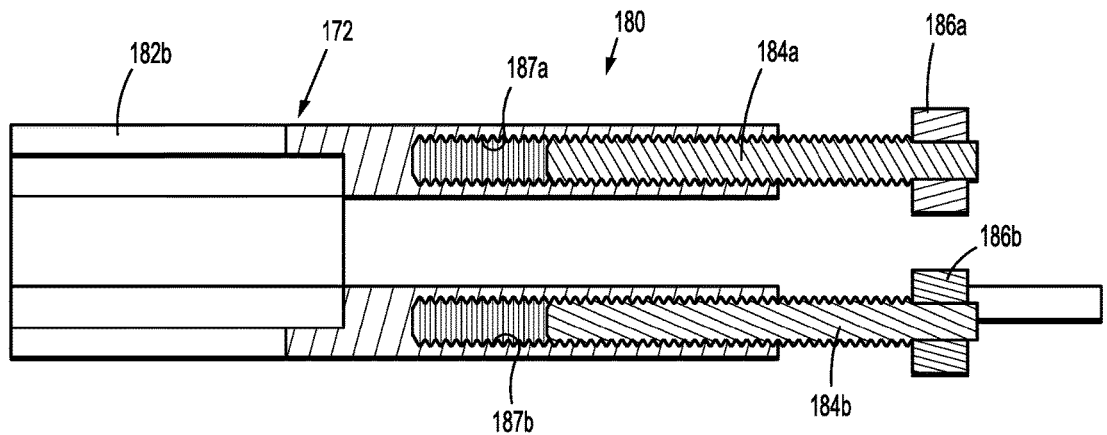
FIG. 11 is a cross-sectional side view of the first pusher assembly of the actuation assembly of FIG. 10, in a second or advanced position.

With additional reference to FIGS. 10 and 11, the second pusher assembly 180 includes the second pusher member 182, first and second drive shafts 184a, 184b operably extendable from a proximal end 182a of the first pusher member 182, and first and second drive gears 186a, 186b supported on respective first and second drive shafts 184a, 184b. In particular, the proximal end 182a of the second pusher member 182 of the first pusher assembly 180 includes first and second extensions or shafts 188a, 188b. The first extension 188a defines a threaded passageway 187a wherein the threads are formed in a first direction for receiving a threaded portion of the first drive shaft 184a and the second extension 188b defines a threaded passageway 187b wherein the threads are formed in a second direction for receiving a threaded portion of the second drive shaft 184b.

With continued reference to FIGS. 10 and 11, the second pusher assembly 180 is disposed within the distal portion 104 (FIG. 6) of the adapter assembly 100 such that the first and second drive gears 186a, 186b on the respective first and second drive shafts 184a, 184b engage the respective first and second drive gears 146 (FIG. 7), 148 of the respective second pair of drive shafts 143 of the third drive assembly 140. As noted above, an idler gear (not shown) engages one of the first and second rotatable flexible drive shafts 142, 144 of the second pair of drive gears 143 to cause the rotation of the first and second rotatable flexible drive shafts 142, 144 in opposite directions, as indicated by arrows "C" and "D" in FIG. 7.

Rotation of the first drive gear 186a in the first direction, simultaneous with rotation of the second drive gear 186b in a second direction, causes longitudinal movement of the second pusher member 182, as indicated by arrow "G" in FIG. 7. More particularly, as the first drive gear 186a rotates the first drive shaft 184a in the first direction and the second drive gear 186b rotates the second drive gear 184b in the second direction, engagement between the threaded first and second drive shafts 184a, 184b and the respective threaded passageways 187a, 187b of the respective first and second extensions 188a, 188b causes the second pusher member 182 to move distally, i.e., advance. Conversely, as the first drive gear 186a rotates the first drive shaft 184a in the second direction and the second drive gear 186b rotates the second drive gear 184b in the first direction, engagement between the threaded first and second drive shafts 184a, 184b and the respective threaded passageways 187a, 187b of the respective first and second extensions 188a, 188b causes the second pusher member 182 to move proximally, i.e., retract.

Distal movement of the second pusher member 182 of the second pusher assembly 180 effects actuation of a loading unit, e.g., loading unit 40 (FIG. 1) of the surgical stapling device 10 (FIG. 1). In one embodiment, distal movement of the second pusher member 182 causes advancement of a knife pusher (not shown) for cutting tissue (not shown). Conversely, proximal movement of the second pusher member 182 of the second pusher assembly 180 returns the second pusher member 182 to its initial position. In some embodiments, proximal movement of the second pusher member 182 permits separation of the loading unit (not shown) from the adapter assembly 100.

The surgical stapling device 10, including adapter assembly 100, operates in a traditional manner. During a surgical stapling procedure, with the anvil assembly 50 of the tool assembly 30 connected to the trocar member 162 of the trocar assembly 160, activation of the first drive assembly 120 causes retraction of the anvil assembly 50 to effect the clamping of tissue (not shown) between an anvil head 52 (FIG. 1) of the anvil assembly 50 and a staple cartridge 42 (FIG. 1) of the loading unit 40. Activation of the second drive assembly 130 causes advancement of the first pusher member 172 of the first pusher assembly 170 to effect the stapling of tissue (not shown) clamped between the anvil head 52 of the anvil assembly 50 and the staple cartridge 42 of the loading unit 40. Activation of the third drive assembly 140 causes advancement of the second pusher member 182 of the second pusher assembly 180 to effect the cutting of tissue (not shown) clamped and stapled between the anvil head 52 of the anvil assembly 50 and the staple cartridge 42 of the loading unit 40.

Following completion of the surgical stapling procedure, the loading unit 40 (FIG. 1) may be separated from the adapter assembly 100, and a new loading unit 40 may be secured to the adapter assembly 100 for further use. It is envisioned that the adapter assembly 100 may be sterilized for use with another patient, wiped clean for re-use on the existing patient, or discarded.

Figure 12:
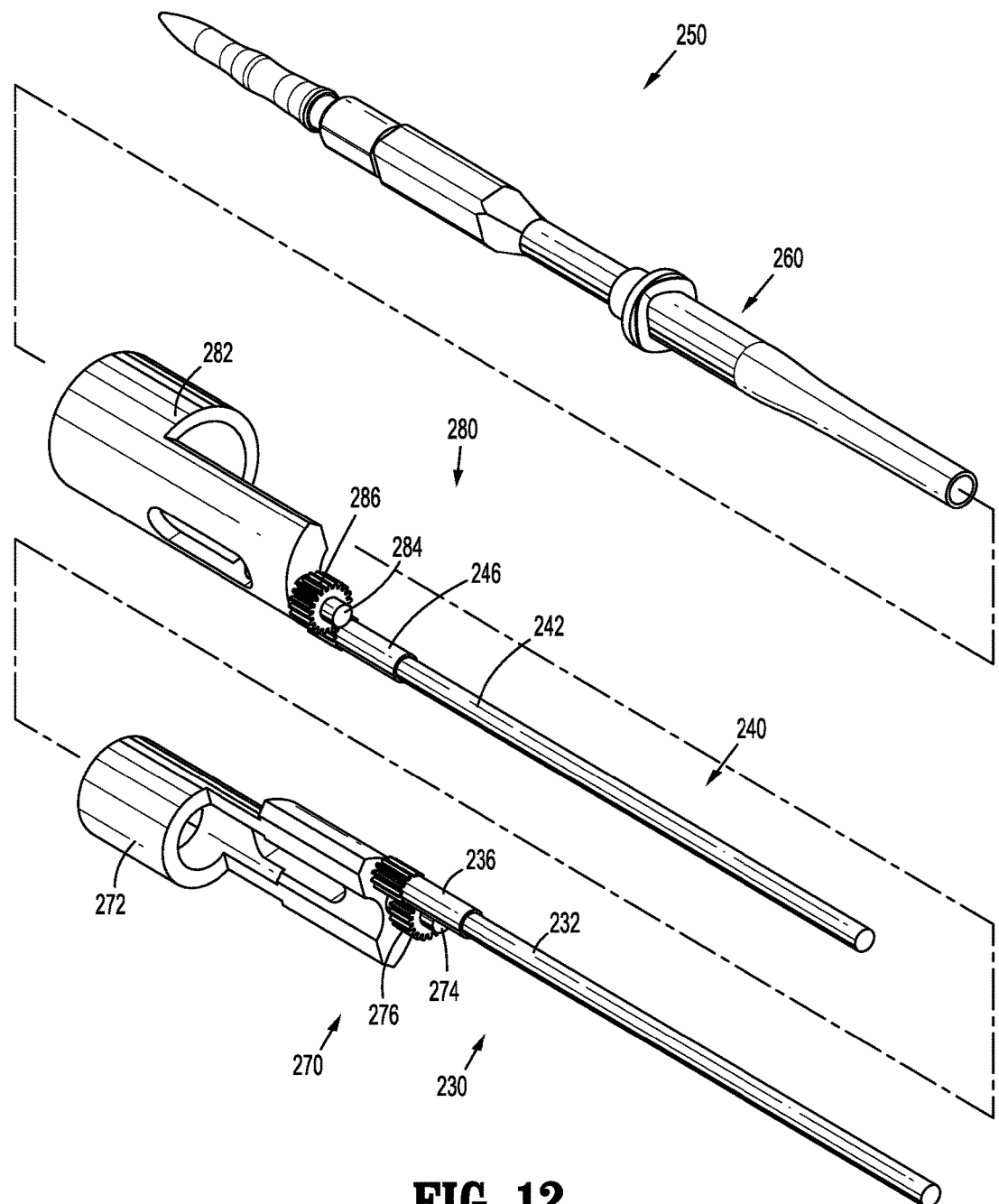
FIG. 12 is a perspective view, with parts separated, of an actuation assembly in accordance with another embodiment of the present disclosure.

With reference now to FIG. 12, an actuation assembly according to an alternative embodiment of the present disclosure is shown generally as actuation assembly 250. The actuation assembly 250 includes a trocar assembly 260, a first pusher assembly 270, and a second pusher assembly 280. The trocar assembly 260 is substantially identical to the trocar assembly 160 (FIG. 7) described hereinabove, and will only be described in detail as relates to the differences therebetween. The first and second pusher assemblies 270 (FIG. 1), 280 (FIG. 1) are substantially similar to the respective first and second pusher assemblies 170, 180 described hereinabove, and will only be described in detail as relates to the differences therebetween.

With continued reference to FIG. 12, the first pusher assembly 270 includes a first pusher member 272, a drive shaft 274 operably extendable from a proximal end 272a of the first pusher member 272, and a drive gear 276 supported on the drive shaft 274. The drive gear 276 of the first pusher assembly 270 is operably engaged by a drive gear 236 of a first rotatable flexible shaft 232 of a second drive assembly 230 to effect rotation of the drive shaft 274. Similarly, the second pusher assembly 280 includes a second pusher member 282, a drive shaft 284 operably extendable from a proximal end 282a of the second pusher member 282, and a drive gear 286 supported on the drive shaft 284. The drive gear 286 of the second pusher assembly 280 is operably engaged by a drive gear 246 of a first rotatable flexible shaft 242 of a third drive assembly 240 to effect rotation of the drive shaft 284.

Although the adapter assembly 100 has been shown and described in relation to operation of the tool assembly 30 (FIG. 1) including the loading unit 40 (FIG. 1) and the anvil assembly 50 (FIG. 1), the adapter assembly 100 may be modified for operation with end effectors having different configurations. For example, the adapter assembly 100 may be modified for use with an end effector having only a single actuation, e.g., linear stapling.

Any of the components described herein may be fabricated from either metals, plastics, resins, composites or the like taking into consideration strength, durability, wearability, weight, resistance to corrosion, ease of manufacturing, cost of manufacturing, and the like.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. An adapter assembly for operably connecting an end effector to a surgical instrument, the adapter assembly comprising:
    a proximal portion configured for operable engagement with a surgical instrument;
    a distal portion configured for operable engagement with an end effector;
    an intermediate portion extending between the proximal portion and the distal portion;
    a drive coupling assembly disposed within the proximal portion;
    a first drive assembly operably connected to the drive coupling assembly, the first drive assembly including a rotatable drive shaft and defining a longitudinal axis;
    a second drive assembly operably connected to the drive coupling assembly, the second drive assembly including a first pair of rotatable drive shafts, each shaft of the first pair of rotatable drive shafts extending between the proximal and distal portions, wherein a first shaft of the first pair of rotatable drive shafts rotates in a first direction and a second shaft of the first pair of rotatable drive shafts rotates in a second direction; and
    a third drive assembly operably connected to the drive coupling assembly, the third drive assembly including a second pair of rotatable drive shafts, each shaft of the second pair of rotatable drive shafts extending between the proximal and distal portions, wherein a first shaft of the second pair of rotatable drive shafts rotates in a first direction and a second shaft of the second pair of rotatable drive shafts rotates in a second direction.

2. The adapter assembly of claim 1, further including a trocar member, wherein rotation of the rotatable drive shaft of the first drive assembly effects longitudinal movement of the trocar member.

3. The adapter assembly of claim 1, further including a first pusher assembly supported in a distal end of the adapter assembly, wherein rotation of the first pair of rotatable drive shafts effects longitudinal movement of the first pusher assembly.

4. The adapter assembly of claim 3, further including a second pusher assembly supported in the distal end of the adapter assembly, wherein rotation of the second pair of rotatable drive shafts effects longitudinal movement of the second pusher assembly.

5. The adapter assembly of claim 4, wherein the second pusher assembly is nested within the first pusher assembly.

6. The adapter assembly of claim 1, wherein the first drive assembly includes a first high ratio transmission assembly.

7. The adapter assembly of claim 6, wherein the second drive assembly includes a second high ratio transmission assembly.

8. The adapter assembly of claim 7, wherein the third drive assembly includes a third high ratio transmission assembly.

9. The adapter assembly of claim 8, wherein the first, second, and third high ratio transmission assemblies are one of a harmonic gear system or a planetary gear system.

10. The adapter assembly of claim 9, wherein the harmonic gear system is one of an orbital gear system or a yoked sun orbital gear system.

11. The adapter assembly of claim 1, further including an outer sleeve, wherein each of the first, second, and third drive assemblies extends through the outer sleeve.

12. The adapter assembly of claim 11, wherein the outer sleeve is flexible.

13. The adapter assembly of claim 1, wherein the coupling assembly is configured for operable connection to a handle assembly.

14. The adapter assembly of claim 1, wherein the first and second shafts of the first pair of rotatable drive shafts of the second drive assembly are radially spaced equidistant from the rotatable drive shaft of the first drive assembly.

15. The adapter assembly of claim 1, wherein the first and second shafts of the second pair of rotatable drive shafts are radially spaced equidistant from the longitudinal axis of the first drive assembly.

16. The adapter assembly of claim 1, wherein an input load from a handle assembly is equally distributed between the first and second shafts of the first pair of rotatable drive shafts during operation of the second drive assembly.

17. The adapter assembly of claim 1, wherein an input load from a handle assembly is equally distributed between the first and second shafts of the second pair of rotatable drive shafts during operation of the third drive assembly.

18. The adapter assembly of claim 1, wherein the first and second pair of rotatable drive shafts are flexible.

19. The adapter assembly of claim 1, wherein each of the first and second pair of rotatable drive shafts forms a helical configuration.

20. An adapter assembly for operably connecting an end effector to a surgical instrument, the adapter assembly comprising:
- a proximal portion configured for operable engagement with a surgical instrument;
- a distal portion configured for operable engagement with an end effector;
- an intermediate portion extending between the proximal portion and the distal portion;
- a drive coupling assembly disposed within the proximal portion;
- a first drive assembly operably connected to the drive coupling assembly, the first drive assembly including a rotatable drive shaft and defining a longitudinal axis; and
- a second drive assembly operably connected to the drive coupling assembly, the second drive assembly including a first pair of rotatable drive shafts, each shaft of the first pair of rotatable drive shafts being flexible and extending between the proximal and distal portions in a helical configuration, wherein a first shaft of the first pair of rotatable drive shafts rotates in a first direction and a second shaft of the first pair of rotatable drive shafts rotates in a second direction.

\* \* \* \* \*